(12) United States Patent
Duce et al.

(10) Patent No.: US 8,766,511 B2
(45) Date of Patent: Jul. 1, 2014

(54) METHOD AND SYSTEM FOR DISTRIBUTED NETWORK OF NANOPARTICLE INK BASED PIEZOELECTRIC SENSORS FOR STRUCTURAL HEALTH MONITORING

(75) Inventors: Jeffrey Lynn Duce, Milton, WA (US); Scott Robert Johnston, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 377 days.

(21) Appl. No.: 13/212,123

(22) Filed: Aug. 17, 2011

(65) Prior Publication Data
US 2013/0044155 A1 Feb. 21, 2013

(51) Int. Cl.
*H01L 41/113* (2006.01)

(52) U.S. Cl.
USPC .............. 310/338; 310/319; 310/328; 73/778

(58) Field of Classification Search
USPC ............ 310/318, 319, 328, 339, 338; 702/39; 73/646, 778
See application file for complete search history.

(56) References Cited

U.S. PATENT DOCUMENTS

| | | | |
|---|---|---|---|
| 6,370,964 B1 * | 4/2002 | Chang et al. | 73/862.046 |
| 8,047,049 B2 * | 11/2011 | Daniel et al. | 73/11.04 |
| 2009/0182515 A1 * | 7/2009 | Pado et al. | 702/36 |
| 2012/0253698 A1 * | 10/2012 | Cokonaj | 702/39 |

FOREIGN PATENT DOCUMENTS

WO   WO-2005069858 A2 *   8/2005

OTHER PUBLICATIONS

Francesca Bortolani et al., "Molten salt synthesis of PZT powder for direct write inks", Journal of the European Ceramic Society 30 (2010) pp. 2073-2079.

K. Byrappa et al., Handbook of Hydrothermal Technology, A Technology for Crystal Growth and Materials Processing, Noyes Publications, Park Ridge, New Jersey, William Andrew Publishing, LLC, Norwich, New York (2001), 12 pages (first page of each chapter).

R.N. Das et al., "In Situ Synthesis of Nanosized PZT Powders in the Precursor Material and the Influence of Particle Size on the Dielectric Property", NanoStructured Materials, vol. 10, No. 8 (1998) pp. 1371-1377.

Yuan Deng et al., "Hydrothermal synthesis and characterization of nanocrystalline PZT powders", Materials Letters 57 (2003) pp. 1675-1678.

Jessie Sungyun Jeon, "Optimization of PZT processing using thermal ink-jet printing", Master's Thesis, Massachusetts Institute of Technology, Jun. 2008, 29 pages.

(Continued)

*Primary Examiner* — Thomas Dougherty

(57) ABSTRACT

The disclosure provides in one embodiment a system for monitoring structural health of a structure. The system has a structure to be monitored for structural health. The system further has a distributed network of nanoparticle ink based piezoelectric sensor assemblies deposited onto the structure. Each assembly has a plurality of nanoparticle ink based piezoelectric sensors and a plurality of conductive ink power and communication wire assemblies interconnecting the plurality of sensors. The system further has an ink deposition apparatus depositing the distributed network of nanoparticle ink based piezoelectric sensor assemblies onto the structure. The system further has an electrical power source providing electrical power to the distributed network. The system further has a data communications network retrieving and processing structural health data of the structure via one or more signals from the sensors.

22 Claims, 8 Drawing Sheets

(56) References Cited

OTHER PUBLICATIONS

Zhong-Cheng Qiu et al., "Hydrothermal synthesis of Pb(Zr0.52Ti0.48)O3 powders at low temperature and low alkaline concentration", Bull. Mater. Sci., vol. 32, No. 2 (2009) pp. 193-197.

B. Su et al., "Control of the particle size and morphology of hydrothermally synthesized lead zirconate titanate powder", Journal of Materials Science 39 (2004) pp. 6439-6447.

Maria Traianidis et al., "Hydrothermal Synthesis of Lead Zirconium Titanate (PZT) Powders and their Characteristics", Journal of the European Ceramic Society 19 (1999) pp. 1023-1026.

S.F. Wang et al., "Characterization of hydrothermally synthesized lead zirconate titanate (PZT) ceramics", Materials Chemistry and Physics 87 (2004) pp. 53-58.

John S. Dodds et al., "Pieozoelectric Characterization of PVDF-TrFE Thin Films Enhanced With ZnO Nanoparticles", IEEE Sensors Journal, vol. 12, No. 6, Jun. 2012, pp. 1889-1890.

Yirong Lin et al., "Enhanced Piezoelectric Properties of Lead Zirconate Titanate Sol-gel Derived Ceramics Using Single Crystal PbZr0.52Ti0.48O3 Cubes", Journal of Applied Physics, 108 (2010), pp. 064108-1 to 064108-6.

Kenneth J. Loh et al., "Zinc Oxide Nanoparticle-Polymeric Thin Films for Dynamic Strain Sensing", Journal of Materials Science, vol. 46 (2011) pp. 228-237.

Zhihong Wang et al., "Dense PZT Thick Films Derived from Sol-gel Based Nanocomposite Process", Materials Science and Engineering, Elsevier, vol. B99 (2003) pp. 56-62.

EPO European Search Report for Counterpart EP Application No. 12175708.2, Nov. 11, 2012, 7 pages.

\* cited by examiner

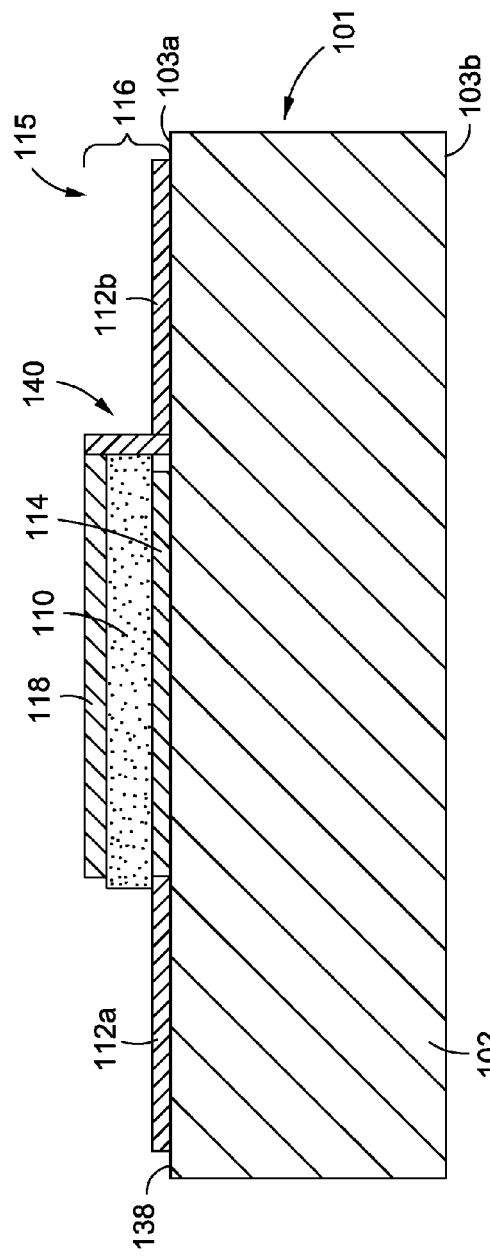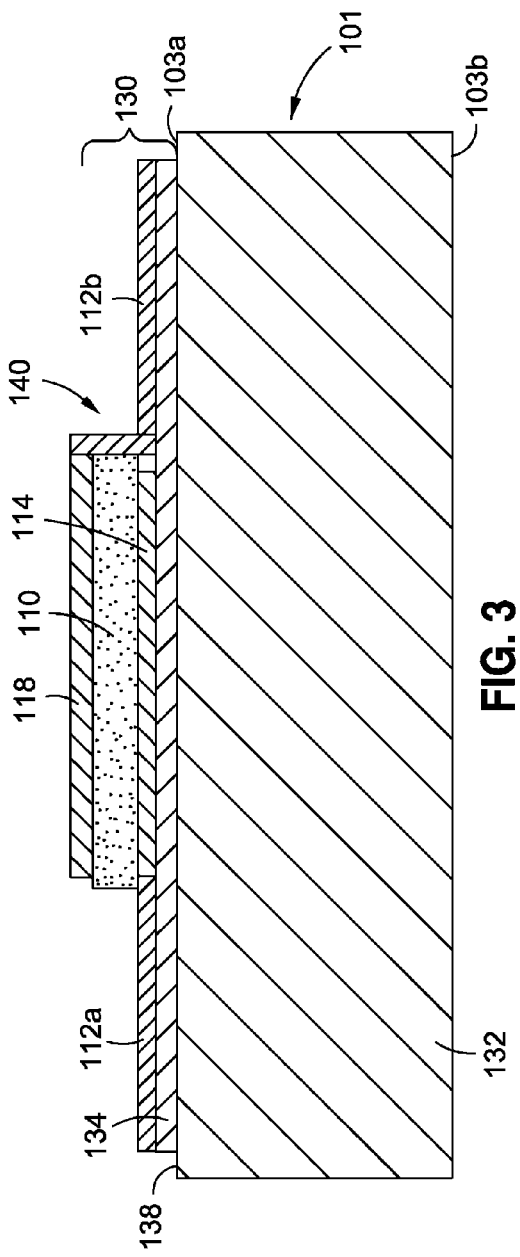

METHOD AND SYSTEM FOR DISTRIBUTED NETWORK OF NANOPARTICLE INK BASED PIEZOELECTRIC SENSORS FOR STRUCTURAL HEALTH MONITORING

CROSS REFERENCE TO RELATED APPLICATIONS

This nonprovisional patent application is related to contemporaneously filed U.S. nonprovisional patent application Ser. No. 13/211,554, titled "METHODS FOR FORMING LEAD ZIRCONATE TITANATE NANOPARTICLES", filed on Aug. 17, 2011, and this nonprovisional patent application is also related to contemporaneously filed U.S. nonprovisional patent application Ser. No. 13/212,037, titled "METHOD AND SYSTEM OF FABRICATING PZT NANOPARTICLE INK BASED PIEZOELECTRIC SENSOR", filed on Aug. 17, 2011. The contents of both of these contemporaneously filed U.S. nonprovisional patent applications are hereby incorporated by reference in their entireties.

BACKGROUND

1) Field of the Disclosure

The disclosure relates generally to structural health monitoring methods and systems, and more particularly, to structural health monitoring methods and systems using nanoparticle sensors deposited onto a surface of a structure.

2) Description of Related Art

Small sensors, such as microsensors, may be used in a variety of applications including in structural health monitoring (SHM) systems and methods to continuously monitor structures, such as composite or metal structures, and to measure material characteristics and stress and strain levels in order to assess performance, possible damage, and current state of the structures. Known SHM systems and methods may include the use of small, stiff, ceramic disk sensors integrated onto a polyimide substrate or other suitable substrate. Such known sensors are typically manually bonded to a structure with an adhesive. Such manual installation may increase labor and installation costs and such adhesive may degrade over time and may result in the sensor disbonding from the structure. In addition, such known sensors may be made of rigid, planar, and/or brittle materials that may limit their usage, for example, usage on a curved or non-planar substrate surface may be difficult. Moreover, such ceramic disk sensors require power and communication wiring with a minimum of two wires connected to each sensor. Such wiring may require connection and management with the use of wire ties, hangars, brackets, or other hardware to maintain organization of the wiring. Such wiring and hardware to manage and organize the wiring may increase the complexity and the weight of the structure.

In addition, known sensor systems and methods, such as micro-electromechanical systems (MEMS) and methods, may include the use of depositing onto a substrate piezoelectric sensors, such as lead zirconate titanate (PZT) sensors, having nanoparticles. Known methods for making such MEMS may include molten salt synthesis of PZT powder for direct write inks. However, the applications of the PZT sensors fabricated with such known methods may be limited by the physical geometry of the PZT sensors. Such physical geometry limitations may result in inadequate sensing capacities or inadequate actuation responses. Further, the PZT sensors fabricated with such known methods may be unable to be applied or located in areas where their function may be important due to the PZT sensor fabrication method. For example, known molten salt synthesis methods may require processing at higher temperatures than certain application substrates can tolerate.

Further, such known MEMS systems and methods may also include the use of sensors having nanoparticles which have not been crystallized and which may be less efficient than nanoparticles which have been crystallized. Non-crystallized structures typically have greater disorganization resulting in decreased response sensitivity to strain and voltage, whereas crystallized structures typically have greater internal organization resulting in increased response sensitivity to strain and decreased necessity for energy to operate. In addition, the nanoparticles of the sensors may be too large for some known deposition processes and systems, such as a jetted atomized deposition (JAD) process, and such nanoparticles may require a high temperature sintering/crystallization process which may result in damage to temperature sensitive substrates or structures.

Accordingly, there is a need in the art for an improved method and system for a distributed network of nanoparticle piezoelectric sensors that may be used in structural health monitoring systems and methods for structures, where such improved method and system provide advantages over known methods and systems.

SUMMARY

This need for an improved method and system for a distributed network of nanoparticle piezoelectric sensors that may be used in structural health monitoring systems and methods for structures is satisfied. As discussed in the below detailed description, embodiments of the system and method may provide significant advantages over existing systems and methods.

In an embodiment of the disclosure, there is provided a system for monitoring structural health of a structure. The system comprises a structure to be monitored for structural health. The system further comprises a distributed network of nanoparticle ink based piezoelectric sensor assemblies deposited onto the structure. Each assembly comprises a plurality of nanoparticle ink based piezoelectric sensors. Each assembly further comprises a plurality of conductive ink power and communication wire assemblies interconnecting the plurality of sensors. The system further comprises an ink deposition apparatus depositing the distributed network of nanoparticle ink based piezoelectric sensor assemblies onto the structure. The system further comprises an electrical power source providing electrical power to the distributed network. The system further comprises a data communications network retrieving and processing structural health data of the structure via one or more signals from the sensors. The structure may have a non-curved or planar surface, a curved or non-planar surface, or a combination of a non-curved or planar surface and a curved or non-planar surface. The nanoparticle ink based piezoelectric sensor assemblies may be deposited onto a surface of the structure with one or more layers of insulation, coatings, or paint in between a body of the structure and the sensor assemblies.

In another embodiment of the disclosure, there is provided a method of monitoring structural health of a structure. The method comprises providing a structure to be monitored for structural health. The method further comprises depositing onto the structure via an ink deposition process a plurality of nanoparticle ink based piezoelectric sensors and a plurality of conductive ink power and communication wire assemblies interconnecting the plurality of sensors to form a distributed network of nanoparticle ink based piezoelectric sensor assemblies. The method further comprises providing electrical power to the distributed network via an electrical power source. The method further comprises using a data communications network to retrieve and process structural health data of the structure via one or more signals from the sensors.

In another embodiment of the disclosure, there is provided a structure to be monitored for structural health. The structure comprises a body. The structure further comprises a distributed network of nanoparticle ink based piezoelectric sensor assemblies deposited onto the body of the structure via an ink deposition process. Each assembly comprises a plurality of nanoparticle ink based piezoelectric sensors. Each assembly further comprises a plurality of conductive ink actuator assemblies interconnecting the plurality of sensors. A signal path within the distributed network comprises a plurality of nanoparticles and structural health data of the structure is obtained via one or more signals from the sensors flowing through the signal path to a data communications network.

In another embodiment of the disclosure, there is provided a method of monitoring structural health of a structure. The method comprises providing a structure to be monitored for structural health. The method further comprises using a distributed network of nanoparticle ink based piezoelectric sensor assemblies to sense and monitor the structural health of the structure. The method further comprises providing electrical power to the distributed network via an electrical power source. The method further comprises using a data communications network to retrieve and process structural health data of the structure via one or more signals from the nanoparticle ink based piezoelectric sensor assemblies sensors.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein:

FIG. 2 is an illustration of a cross-sectional view of one of the embodiments of a deposited nanoparticle ink based piezoelectric sensor assembly;

FIG. 3 is an illustration of a cross-sectional view of another one of the embodiments of a deposited nanoparticle ink based piezoelectric sensor assembly;

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art. The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
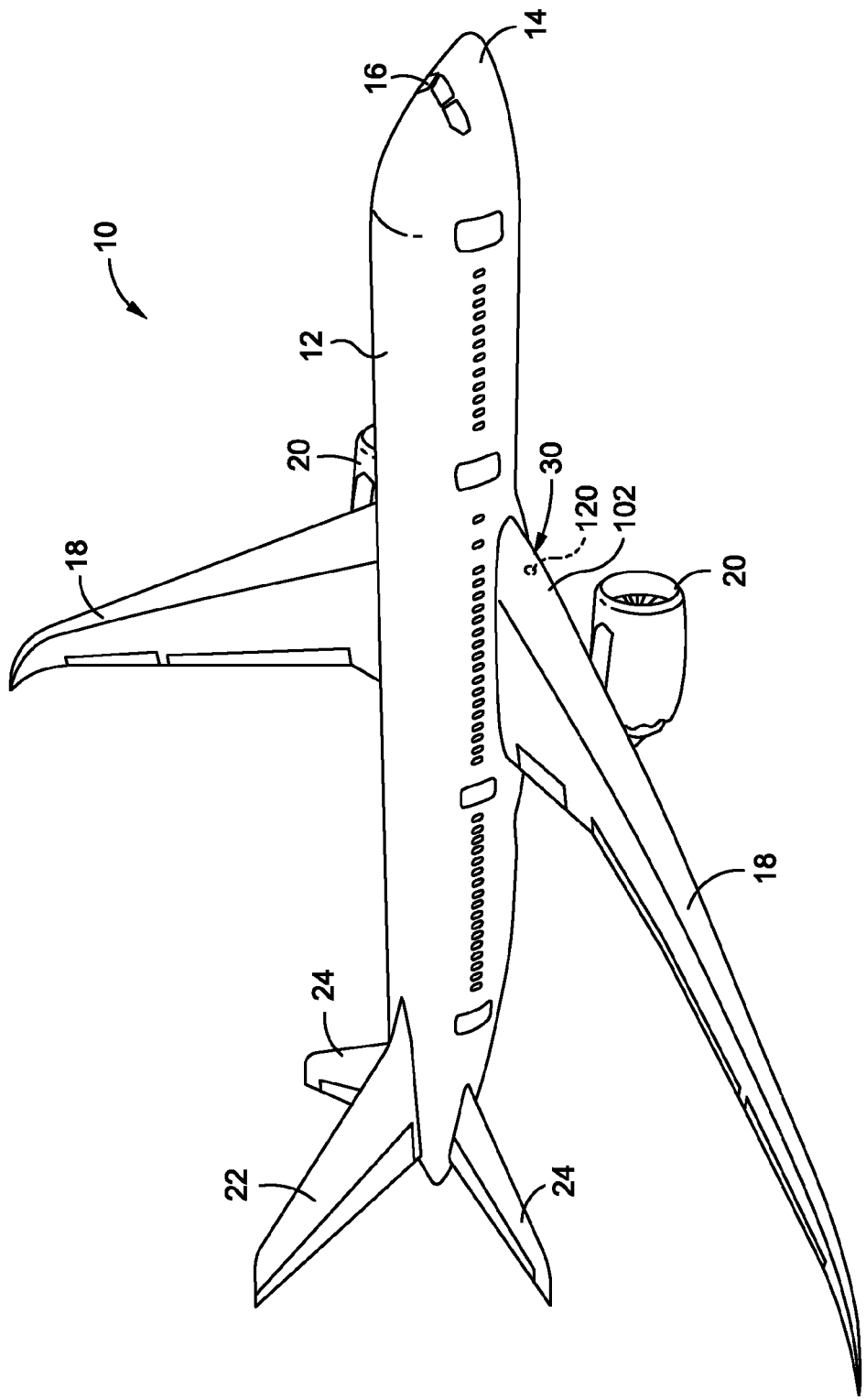
FIG. 1 is an illustration of a perspective view of an exemplary aircraft for which one of the embodiments of the system and method of the disclosure may be used.

Now referring to the Figures, FIG. 1 is an illustration of a perspective view of an exemplary prior art aircraft 10 for which one of the embodiments of a distributed network of nanoparticle ink based piezoelectric sensor assemblies 120 (see FIG. 5) of a structure 30 may be used, as well as for which a system 170 (see FIG. 7) and a method 200 (see FIG. 8) for structural health monitoring using nanoparticle ink based piezoelectric sensors 110 (see FIGS. 2-4) may be used. The aircraft 10 comprises a fuselage 12, a nose 14, a cockpit 16, wings 18 operatively coupled to the fuselage 12, one or more propulsion units 20, a tail vertical stabilizer 22, and one or more tail horizontal stabilizers 24. Although the aircraft 10 shown in FIG. 1 is generally representative of a commercial passenger aircraft, the system 170 and method 200 disclosed herein may also be employed in other types of aircraft. More specifically, the teachings of the disclosed embodiments may be applied to other passenger aircraft, cargo aircraft, military aircraft, rotorcraft, and other types of aircraft or aerial vehicles, as well as aerospace vehicles such as satellites, space launch vehicles, rockets, and other types of aerospace vehicles. It may also be appreciated that embodiments of systems, methods and apparatuses in accordance with the disclosure may be utilized in other vehicles, such as boats and other watercraft, trains, automobiles, trucks, buses, and other types of vehicles. It may also be appreciated that embodiments of systems, methods and apparatuses in accordance with the disclosure may be utilized in architectural structures, turbine blades, medical devices, electronic actuation equipment, consumer electronic devices, vibratory equipment, passive and active dampers, or other suitable structures.

Figure 7:
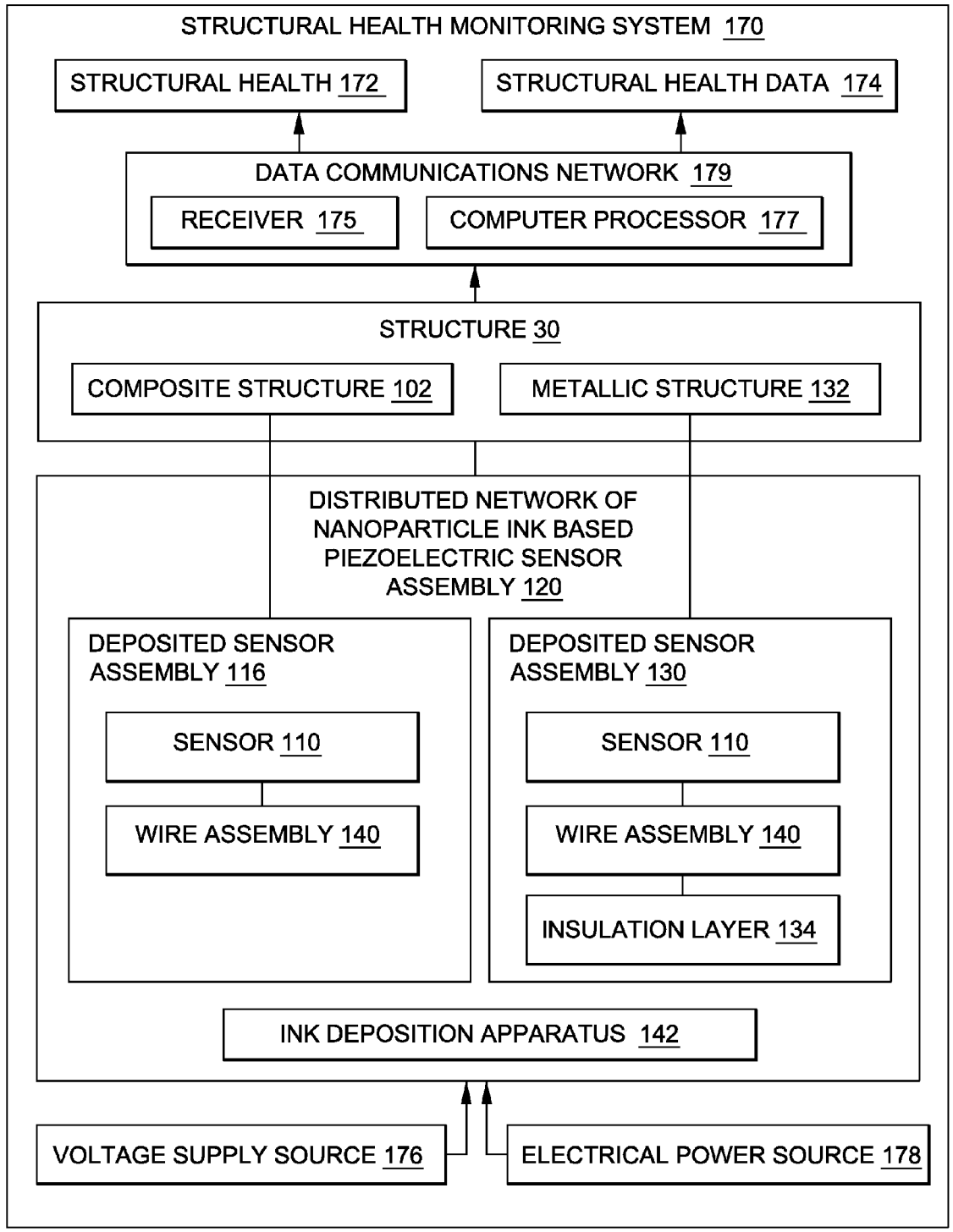
FIG. 7 is an illustration of a schematic diagram of one of the embodiments of a structural health monitoring system using the distributed network of nanoparticle ink based piezoelectric sensor assemblies of the disclosure.

As shown in FIG. 7, in an embodiment of the disclosure, there is provided a structural health monitoring system 170 for monitoring structural health 172 of a structure 30. FIG. 7 is an illustration of a block diagram of one of the embodiments of the structural health monitoring system 170 using the nanoparticle ink based piezoelectric sensors 110 of the disclosure. The system 170 comprises a structure 30 to be monitored for structural health 172. The system 170 further comprises a distributed network of nanoparticle ink based piezoelectric sensor assemblies 120 deposited onto a surface of the structure 30. The distributed network of nanoparticle ink based piezoelectric sensor assemblies 120 may be deposited onto a surface of the structure 30 with one or more layers of insulation, coatings, or paint in between a body 32 (see FIG. 5) of the structure 30 and the distributed network of nanoparticle ink based piezoelectric sensor assemblies 120.

Each sensor assembly 120 comprises a plurality of nanoparticle ink based piezoelectric sensors 110. Each sensor assembly 120 further comprises a plurality of conductive ink power and communication wire assemblies 140, acting as actuator assemblies 141, interconnecting the plurality of nanoparticle ink based piezoelectric sensors 110. The structural health monitoring system 170 preferably comprises a deposited nanoparticle ink based piezoelectric sensor assembly 115 (see also FIGS. 2 and 3). In one embodiment the deposited nanoparticle ink based piezoelectric sensor assembly 115 may comprise a deposited nanoparticle ink based piezoelectric sensor assembly 116 (see FIG. 2), if used with the composite structure 102, and may comprise a deposited nanoparticle ink based piezoelectric sensor assembly 130 (see FIG. 3), if used with a metallic structure 132. As shown in FIG. 7, the structural health monitoring system 170 further comprises an ink deposition apparatus 142 depositing the distributed network of nanoparticle ink based piezoelectric sensor assemblies 120 onto a surface of the structure 30. The structural health monitoring system 170 may further comprise a voltage supply source 176 for poling the plurality of sensors 110. The voltage supply source 176 may be used for poling the nanoparticle ink based piezoelectric sensors 110 prior to use in the structural health monitoring system 170. As used herein, the term "poling" means a process by which a strong electric field is applied across a material, usually at elevated temperatures, in order to orient or align dipoles or domains. The voltage supply source 176 may also drive some piezoelectric sensors 110 so that they become actuators 141 sending interrogating signals to other piezoelectric sensors 110.

As shown in FIG. 7, the structural health monitoring system 170 further comprises an electrical power source 178 providing electrical power to the sensor assembly 120. The electrical power source 178 may comprise batteries, voltage, RFID (radio frequency identification), magnetic induction transmission, or another suitable electrical power source. The electrical power source 178 may be wireless. As shown in FIG. 7, the structural health monitoring system 170 further comprises a data communications network 179 for retrieving and processing structural health data 174 of the structure 30 via one or more signals 92 from the sensors 110. The data communications network 179 may be wireless. The data communications network 179 may be digital or analog. The data communications network 179 may retrieve data received from the nanoparticle ink based piezoelectric sensors 110, such as with a receiver 175 (see FIG. 7), and may process data received from the nanoparticle ink based piezoelectric sensors 110, such as with a computer processor 177 (see FIG. 7). The data communications network 179 may be wireless.

The deposition of the nanoparticle ink based piezoelectric sensors 110 onto a surface of the substrate 101 or onto a surface of the structure 30 (see FIG. 7) enables in situ installation of the nanoparticle ink based piezoelectric sensors 110 for applications such as structural health monitoring. The nanoparticle ink based piezoelectric sensors 110 may be a key enabler of high density structural health monitoring systems 170. Two or more nanoparticle ink based piezoelectric sensors 110 may be used to enable the structural health monitoring system 170 for monitoring structural health 172 of a structure 30, such as a composite structure 102 (see FIG. 1) or a metallic structure 132 (see FIG. 3), or another suitable structure, and for providing structural health data 174. The structural health data 174 may comprise disbonds, weak bonding, strain levels, moisture ingression, materials change, cracks, voids, delamination, porosity, or other suitable structural health data 174 or electromechanical properties or other irregularities which may adversely affect the performance of the structure 30.

Figure 9:
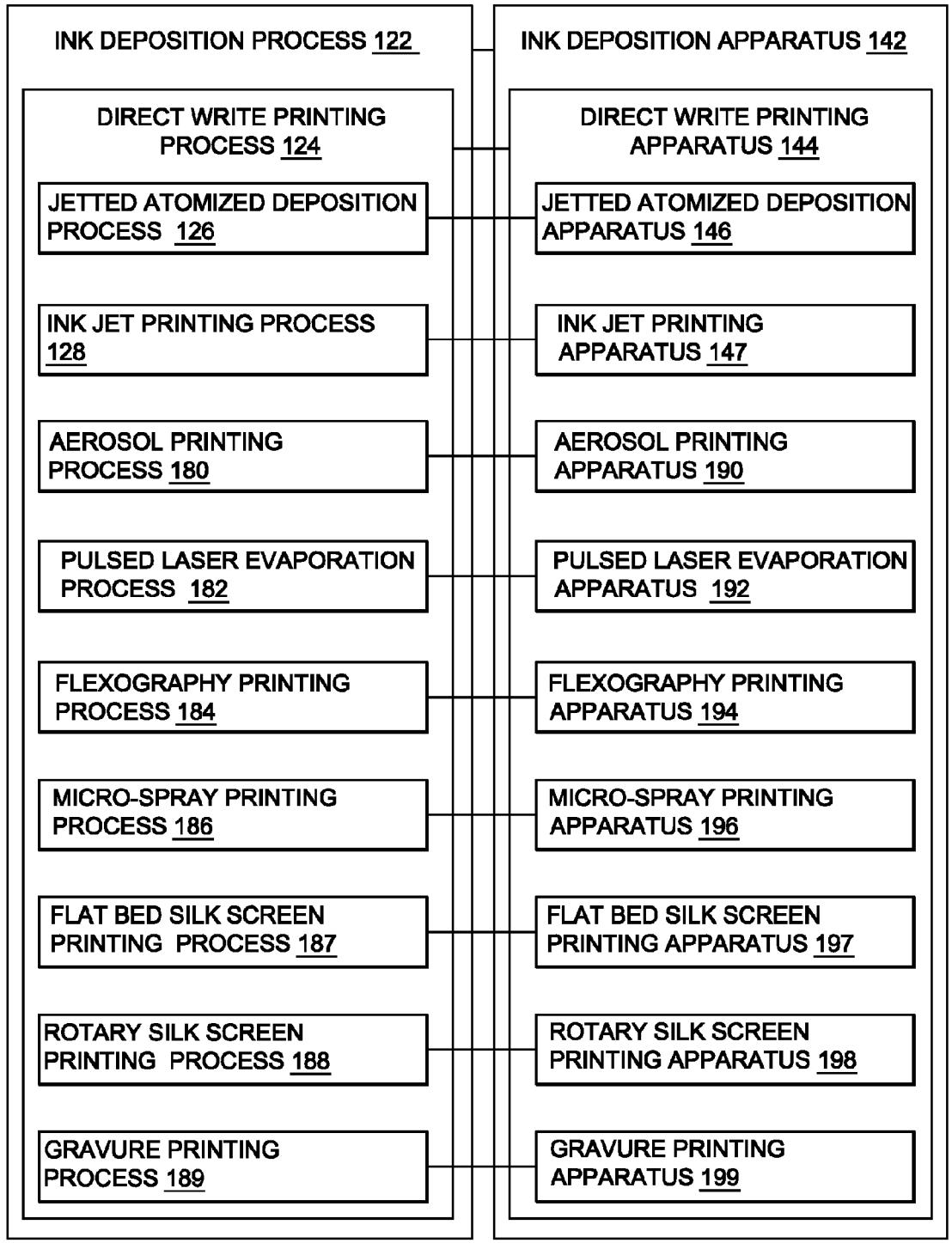

The structure 30 preferably comprises a material comprising a composite material, a metallic material, or a combination of a composite material and a metallic material. The structure 30 preferably has a curved surface 138 on which the distributed network of nanoparticle ink based piezoelectric sensor assemblies 120 is deposited. The nanoparticle ink based piezoelectric sensors 110 may be deposited onto the structure 30 in a customized shape 164 (see FIG. 6B). As shown in FIG. 9, the ink deposition apparatus 142 may comprise a direct write printing apparatus 144 comprising a jetted atomized deposition apparatus 146, an ink jet printing apparatus 147, an aerosol printing apparatus 190, a pulsed laser evaporation apparatus 192, a flexography printing apparatus 194, a micro-spray printing apparatus 196, a flat bed silk screen printing apparatus 197, a rotary silk screen printing apparatus 198, a gravure printing apparatus 199, or another suitable direct write printing apparatus 144. The distributed network of nanoparticle ink based piezoelectric sensor assemblies 120 may further comprise an insulation layer 134 deposited onto a surface of the structure 30. As shown in FIGS. 2 and 3, the conductive ink power and communication wire assemblies 140 preferably comprise a first conductive electrode 114, a second conductive electrode 118, a first conductive trace wire 112a, and a second conductive trace wire 112b. The structural health data 174 may comprise disbonds, weak bonding, strain levels, moisture ingression, materials change, cracks, voids, delamination, porosity, and irregularities that adversely affect the performance of the structure 30. The nanoparticle ink based piezoelectric sensors 110 are preferably comprised of nanoparticles having a particle size in a range of from about 20 nanometers to about 1 micron. The structure 30 preferably comprises an aircraft structure 10 (see FIG. 1).

Figure 5:
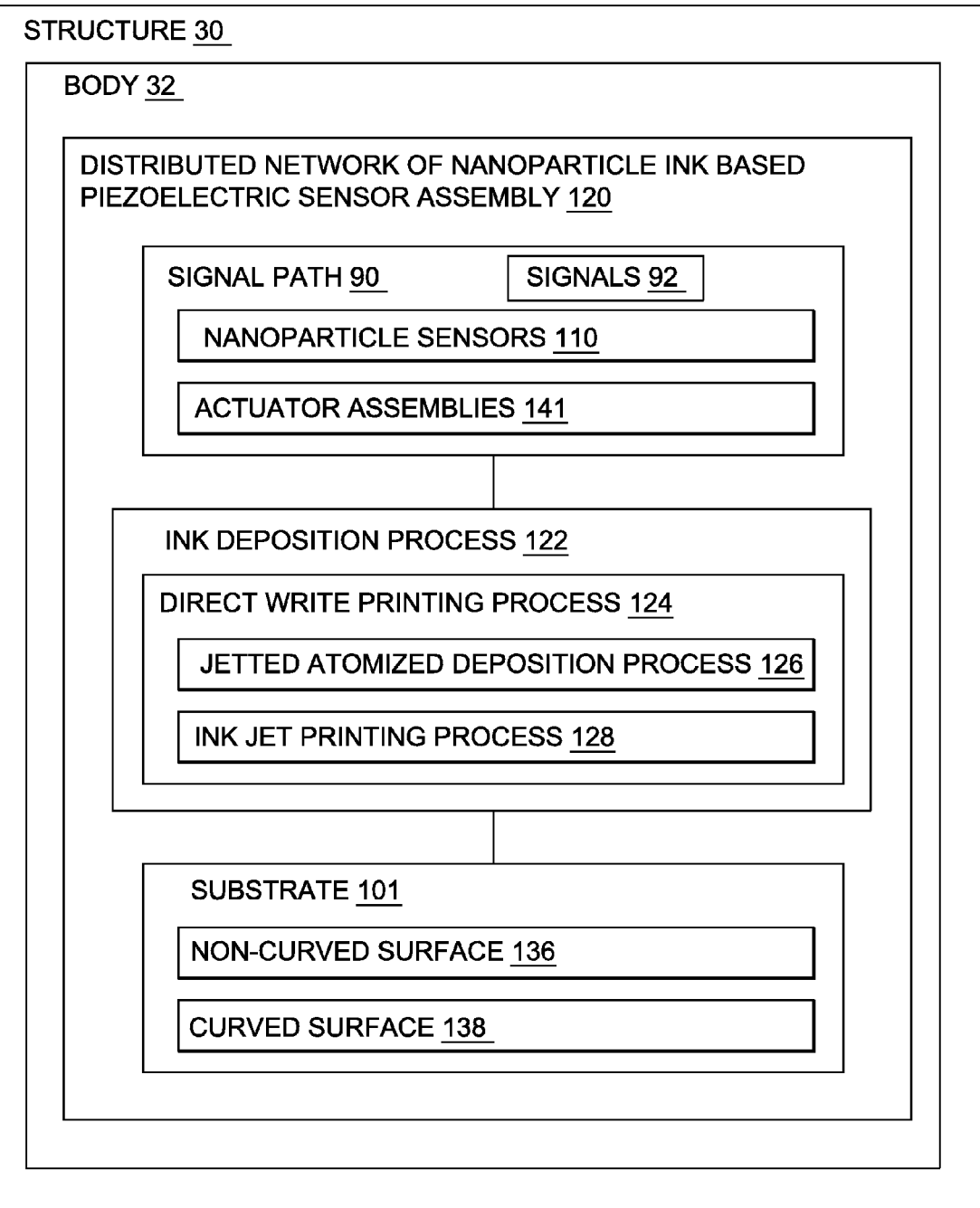
FIG. 5 is an illustration of a block diagram of one of the embodiments of a structure having a distributed network of nanoparticle ink based piezoelectric sensor assemblies of the disclosure.

As shown in FIG. 5, in another embodiment of the disclosure, there is provided a structure 30 to be monitored for structural health 172 (see FIG. 7). FIG. 5 is an illustration of a block diagram of one of the embodiments of the structure 30 of the disclosure. The structure 30 comprises a body 32. The structure 30 further comprises a distributed network of nanoparticle ink based piezoelectric sensor assemblies 120 deposited onto a surface of the structure 30 via an ink deposition process 122. Each sensor assembly 120 comprises a plurality of nanoparticle ink based piezoelectric sensors 110. Each sensor assembly 120 further comprises a plurality of conductive ink actuator assemblies 141 interconnecting the plurality of nanoparticle ink based piezoelectric sensors 110. A signal path 90 within the sensor assembly 120 comprises a plurality of nanoparticles. Structural health data 174 (see FIG. 7) of the structure 30 is preferably obtained via one or more signals 92 from the nanoparticle ink based piezoelectric sensors 110 flowing through the signal path 90 to a data communications network 179 (see FIG. 7).

The nanoparticle ink based piezoelectric sensors 110 may comprise a nanoparticle ink such as a formulated lead zirconate titanate (PZT) ink, barium titanate ($BaTiO_3$), or another suitable nanoparticle ink. The ink preferably comprises nanoscale ink nanoparticles. Preferably, the nanoscale ink nanoparticles are pre-crystallized. The nanoparticle ink preferably has a nanoscale particle size in a range of from about 20 nanometers to about 1 micron. The nanoscale ink particles size allows for the nanoparticle ink to be deposited using a wide range of ink deposition processes, apparatuses, and systems, and in particular, allows for the nanoparticle ink to be deposited using a jetted atomized deposition process 126 (see FIGS. 6A and 9) and a jetted atomized deposition apparatus 146 (see FIGS. 6A and 9). Each of the nanoparticle ink based piezoelectric sensor 110 may have a thickness in a range of from about 1 micron to about 500 microns. The thickness of the nanoparticle ink based piezoelectric sensors 110 may be measured in terms of a factor of nanoparticle size of the nanoparticles and the thickness of first and second conductive electrodes 114, 118 (see FIG. 2). Thickness of the nanoparticle ink based piezoelectric sensor 110 may also depend on the size of the nanoparticle ink based piezoelectric sensor 110, as a proper aspect ratio may increase the sensitivity of the nanoparticle ink based piezoelectric sensor 110.

The nanoparticle ink 104 may further comprise an adhesion promoter, such as a sol-gel based adhesion promoter, a polymer based adhesion promoter such as an epoxy or another suitable polymer based adhesion promoter, or another suitable adhesion promoter for promoting adhesion of the nanoparticle ink to a surface of the substrate 101 (see FIG. 5). In one embodiment the nanoscale ink nanoparticles may be suspended in a silica sol-gel and then deposited using an ink deposition process 122 such as a direct write printing process 124 (see FIG. 9). The silica sol-gel in the nanoparticle ink formulation enables the nanoparticle ink to bond to a wider variety of substrates than certain known adhesion promoters. The nanoparticle ink based piezoelectric sensor 110 preferably has modalities based on ultrasonic wave propagation and electromechanical impedance.

Lead zirconate titanate (PZT) nanoparticle ink may be formulated by methods disclosed in contemporaneously filed U.S. nonprovisional patent application Ser. No. 13/211,554, titled "METHODS FOR FORMING LEAD ZIRCONATE TITANATE NANOPARTICLES", filed on Aug. 17, 2011, which is hereby incorporated by reference in its entirety.

As shown in FIG. 5, the substrate 101 may have a non-curved or planar surface 136, a curved or non-planar surface 138, or a combination of a non-curved or planar surface 136 and a curved or non-planar surface 138. As shown in FIG. 2, the substrate 101 may have a first surface 103*a* and a second surface 103*b*. The substrate 101 preferably comprises a composite material, a metallic material, a combination of a composite material and a metallic material, or another suitable material. As shown in the FIG. 2, the substrate 101 may comprise a composite structure 102. The composite structure 102 may comprise composite materials such as polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. As shown in FIG. 3, the substrate 101 may comprise a metallic structure 132. The metallic structure 132 may comprise metal materials such as aluminum, stainless steel, titanium, alloys thereof, or another suitable metal or metal alloy. The substrate 101 may also comprise another suitable material.

Figure 6:
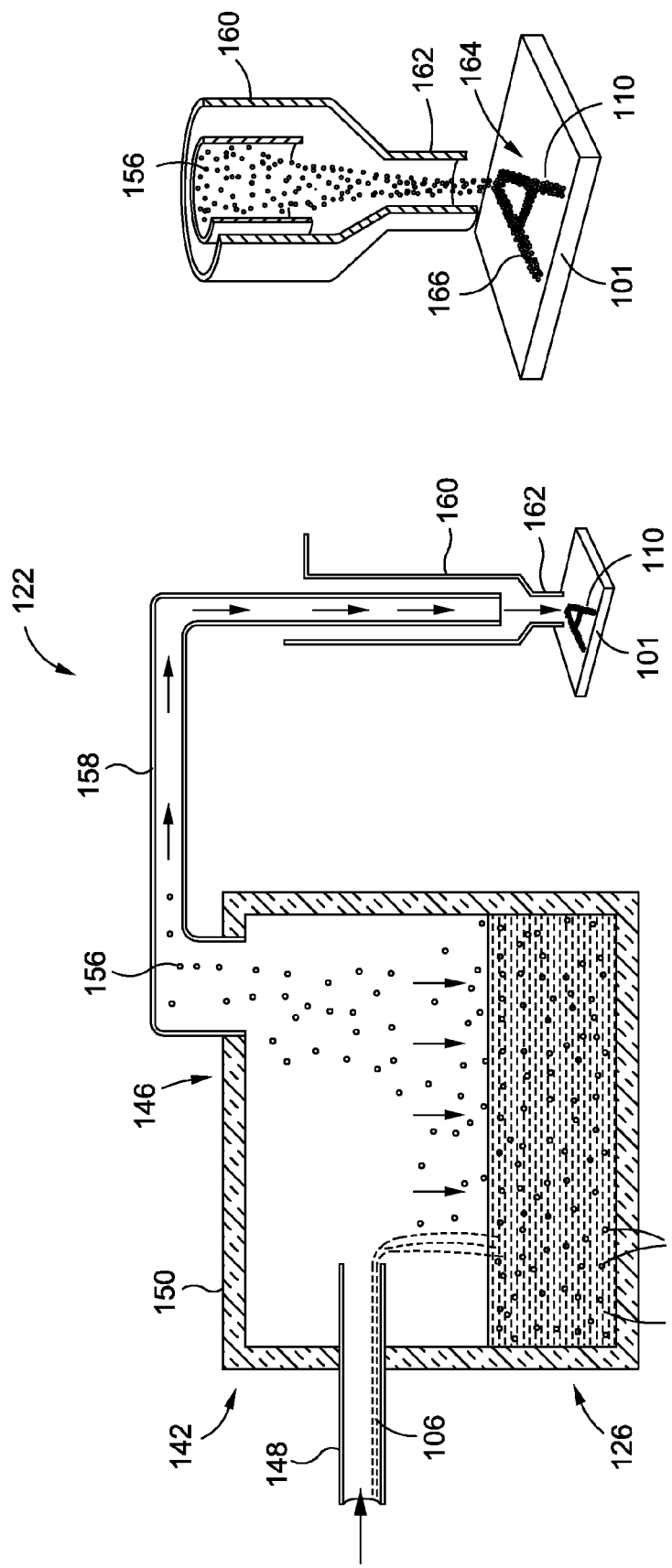
FIG. 6A is an illustration of a schematic view of one of the embodiments of an ink deposition process and apparatus for fabricating a nanoparticle ink based piezoelectric sensor of the disclosure.
FIG. 6B is an illustration of a close-up view of the piezoelectric nanoparticle ink based sensor being deposited onto the surface of a substrate.

FIG. 6A is an illustration of a schematic view of one of the embodiments of an ink deposition process 122 and an ink deposition apparatus 142 for fabricating the nanoparticle ink based piezoelectric sensors 110 of the disclosure. An exemplary direct write printing process 124 and direct write printing apparatus 144 are shown in FIG. 6A, which shows the jetted atomized deposition process 126 and the jetted atomized deposition apparatus 146. As shown in FIG. 6A, nanoscale ink nanoparticles 106 may be transferred via an inlet 148 into a mixing vessel 150 containing a solvent 152. The nanoscale ink nanoparticles 106 are preferably mixed with the solvent 152 in the mixing vessel to form a nanoparticle ink suspension 154. The nanoparticle ink suspension 154 may be atomized by an ultrasonic mechanism 158 to form atomized ink nanoparticles 156. The atomized ink nanoparticles 156 may then be transferred through a nozzle body 160 and directed through a nozzle tip 162 to the surface of the substrate 101 for depositing and printing of the nanoparticle ink based piezoelectric sensors 110 onto the substrate 101.

FIG. 6B is an illustration of a close-up view of the piezoelectric nanoparticle ink based sensors 110 being deposited onto the surface of the substrate 101. FIG. 6B shows the atomized ink nanoparticles 156 in the nozzle body 160 and the nozzle tip 162 being deposited onto the substrate 101 to form the piezoelectric nanoparticle ink based sensors 110. As shown in FIG. 6B, the nanoparticle ink based piezoelectric sensors 110 may be deposited onto the substrate 101 in a customized shape 164, such as letters, designs, logos, or insignias, or geometric shapes, such as circles, squares, rectangles, triangles, or other geometric shapes, or another desired customized shape 164. The ink deposition process 122 and the ink deposition apparatus 142 do not require growth of crystals 166 on the substrate 101. Moreover, the deposited nanoscale ink nanoparticles 106 contain a crystalline particle structure that does not require any post processing steps to grow the crystals.

FIGS. 2 and 3 show embodiments of a deposited nanoparticle ink based piezoelectric sensor assembly 115. FIG. 2 is an illustration of a cross-sectional view of one of the embodiments of a deposited nanoparticle ink based piezoelectric sensor assembly 116 that is deposited onto a substrate 101 comprising a composite structure 102. The deposited nanoparticle ink based piezoelectric sensor assembly 116 comprises the nanoparticle ink based piezoelectric sensor 110 coupled to a power and communication wire assembly 140 acting as an actuator assembly 141 (see FIG. 4). The power and communication wire assembly 140 is preferably formed of a conductive ink 168 (see FIG. 4) that may be deposited via the ink deposition apparatus 142 and via the ink deposition process 122 onto the substrate 101. The power and communication wire assembly 140 acting as an actuator assembly 141 (see FIG. 4) may comprise a first conductive electrode 114, a second conductive electrode 118, a first conductive trace wire 112*a*, and a second conductive trace wire 112*b*. The first conductive electrode 114, the second conductive electrode 118, the first conductive trace wire 112*a*, and the second conductive trace wire 112*b* may be adjacent to the nanoparticle ink based piezoelectric sensor 110.

FIG. 3 is an illustration of a cross-sectional view of another one of the embodiments of a deposited nanoparticle ink based piezoelectric sensor assembly 130 that is deposited onto a substrate 101 comprising a metallic structure 132. The deposited nanoparticle ink based piezoelectric sensor assembly 130 comprises the nanoparticle ink based piezoelectric sensor 110 coupled to a power and communication wire assembly 140 acting as an actuator assembly 141 (see FIG. 4). The power and communication wire assembly 140 is preferably formed of a conductive ink 168 (see FIG. 4) that may be deposited via the ink deposition apparatus 142 and via the ink deposition process 122 onto the substrate 101. The power and communication wire assembly 140 acting as an actuator assembly 141 may comprise the first conductive electrode 114, the second conductive electrode 118, the first conductive trace wire 112*a*, and the second conductive trace wire 112*b*. The first conductive electrode 114, the second conductive electrode 118, the first conductive trace wire 112*a*, and the second conductive trace wire 112*b* may be adjacent to the nanoparticle ink based piezoelectric sensor 110. As shown in FIG. 3, the deposited nanoparticle ink based piezoelectric sensor assembly 130 further comprises an insulation layer 134 deposited directly onto the body of the substrate 101, the substrate 101 comprising the metallic structure 132. The nanoparticle ink based piezoelectric sensor 110 may be deposited over the insulation layer 134. The insulation layer 134 may comprise an insulating polymer coating, a dielectric material, a ceramic material, a polymer material, or another suitable insulation material. The nanoparticle ink based piezoelectric sensor 110 is preferably coupled to the power and communication wire assembly 140.

Figure 4:
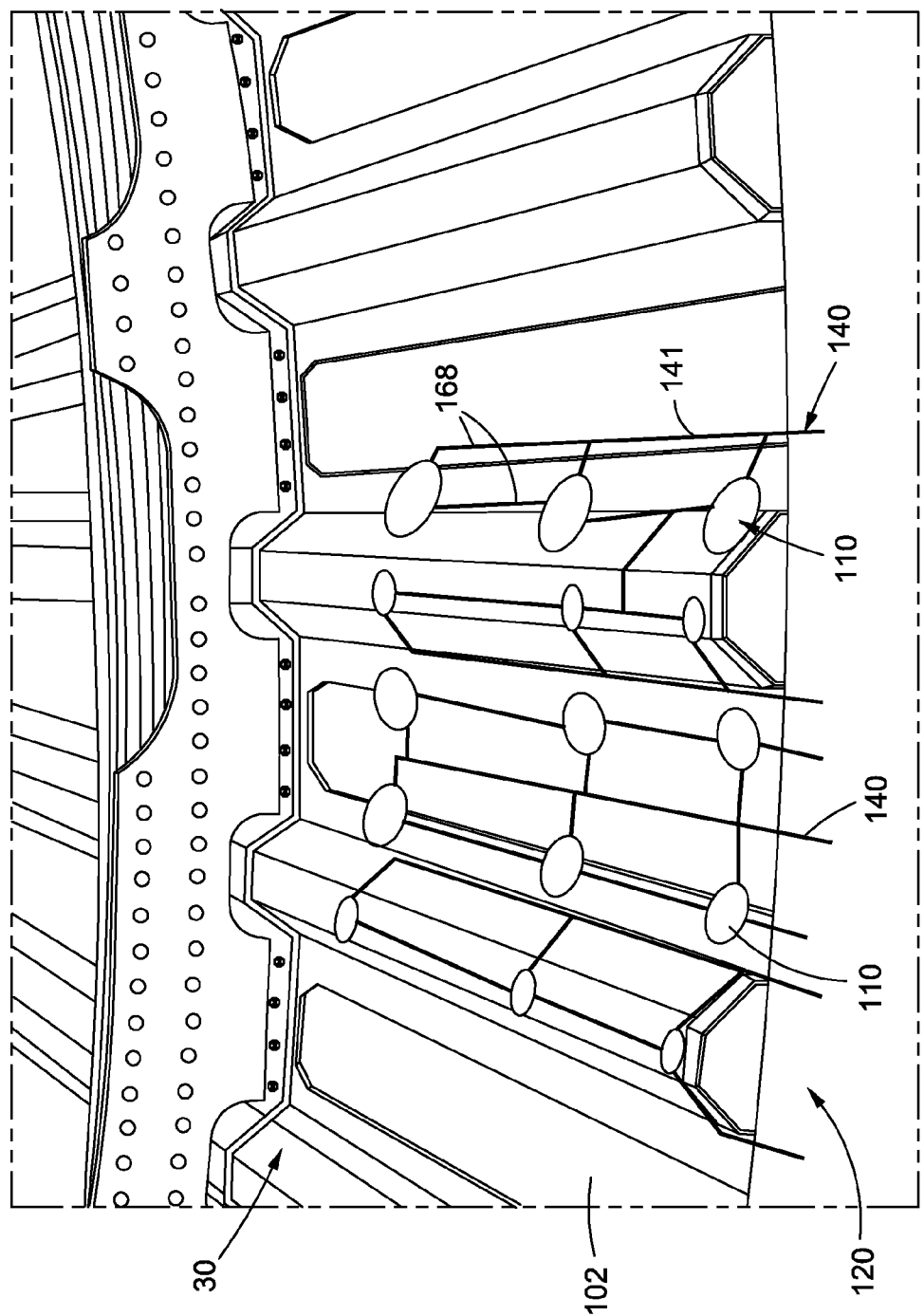
FIG. 4 is an illustration of a top perspective view of one of the embodiments of a deposited distributed network of nanoparticle ink based piezoelectric sensor assemblies.

FIG. 4 is an illustration of a top perspective view of the distributed network of nanoparticle ink based piezoelectric sensor assemblies 120. FIG. 4 shows a plurality of the nanoparticle ink based piezoelectric sensors 110 coupled to the plurality of conductive ink 168 power and communication wire assemblies 140 acting as actuator assemblies 141, all deposited on the structure 30, such as the composite structure 102. Similarly, for a metallic structure 132, a plurality of nanoparticle ink based piezoelectric sensors 110 may be coupled to a plurality of power and communication wire assemblies 140, all deposited on the metallic structure 132.

Figure 8:
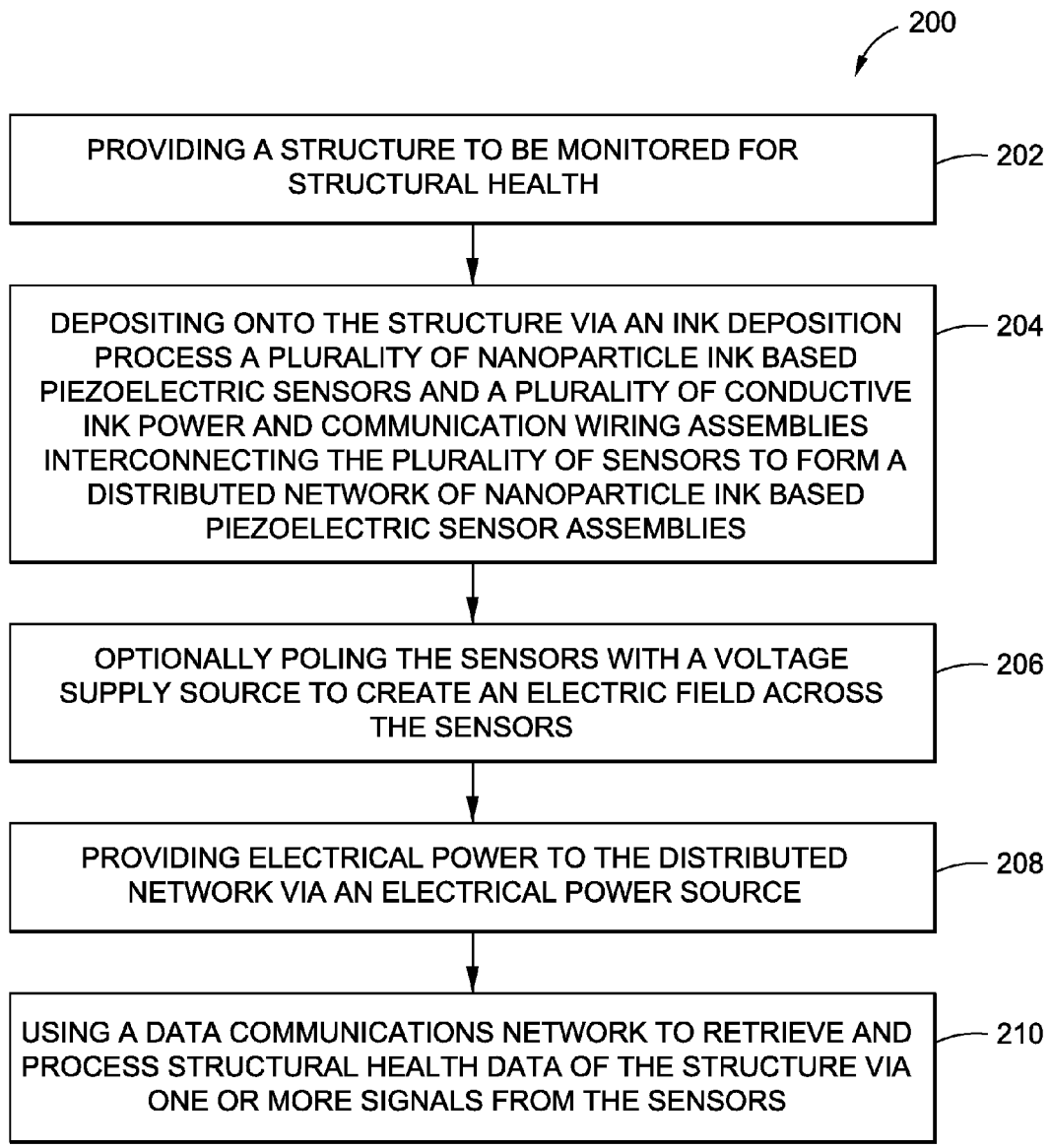
FIG. 8 is an illustration of a flow diagram of an embodiment of a method of the disclosure; and, FIG. 9 is an illustration of a block diagram of embodiments of the ink deposition processes and ink deposition apparatuses that may be used in the system and method disclosed herein.

In another embodiment of the disclosure, there is provided a method 200 of monitoring structural health of a structure 30. FIG. 8 is an illustration of a flow diagram of an embodiment of the method 200 of the disclosure. The method 200 comprises step 202 of providing a structure 30 to be monitored for structural health 172 (see FIG. 7). The method 200 further comprises step 204 of depositing onto the structure 30 via an ink deposition process 122 a plurality of nanoparticle ink based piezoelectric sensors 110 and a plurality of conductive ink power and communication wire assemblies 140 interconnecting the plurality of sensors 110 to form a distributed network of nanoparticle ink based piezoelectric sensor assemblies 120.

As shown in FIG. 8, the method 200 further comprises optional step 206 of poling the nanoparticle ink based piezoelectric sensors 110 with a voltage supply source 176 (see FIG. 7) to create an electric field across the nanoparticle ink based piezoelectric sensors 110. The method 200 further comprises step 208 of providing electrical power to the distributed network of nanoparticle ink based piezoelectric sensor assemblies 120 via an electrical power source 178 (see FIG. 7). The method 200 further comprises step 210 of using a data communications network 179 (see FIG. 7) to retrieve and process structural health data 174 (see FIG. 7) of the structure 30 via one or more signals 92 (see FIG. 5) from the nanoparticle ink based piezoelectric sensors 110.

The structure 30 preferably comprises an aircraft structure 10 (see FIG. 1). As shown in FIG. 9, the ink deposition process 122 may comprise a direct write printing process 124 comprising a jetted atomized deposition process 126, an ink jet printing process 128, an aerosol printing process 180, a pulsed laser evaporation process 182, a flexography printing process 184, a micro-spray printing process 186, a flat bed silk screen printing process 187, a rotary silk screen printing process 188, a gravure printing process 189, or another suitable direct write printing process 124. The data communications network 179 may retrieve structural health data 174 received from the nanoparticle ink based piezoelectric sensors 110 with a receiver 175 (see FIG. 7) and may process structural health data 174 received from the nanoparticle ink based piezoelectric sensors 110 with a computer processor 177 (see FIG. 7). The structural health data 174 may comprise disbonds, weak bonding, strain levels, moisture ingression, materials change, cracks, voids, delamination, porosity, and irregularities that adversely affect the performance of the structure, or other suitable structural health data 174.

The substrate 101 preferably comprises a composite material, a metallic material, a combination of a composite material and a metallic material, or another suitable material. The substrate 101 preferably comprises a first surface 103*a* and a second surface 103*b* (see FIG. 2). The substrate 101 may have a non-curved or planar surface 136 (see FIG. 5), a curved or non-planar surface 138 (see FIG. 5), or a combination of a non-curved or planar surface 136 (see FIG. 5) and a curved or non-planar surface 138 (see FIG. 5). The nanoparticle ink based piezoelectric sensors 110 may be deposited onto the substrate 101 in a customized shape 164 (see FIG. 6B).

The nanoparticle ink based piezoelectric sensors 110 may undergo a poling process with a voltage supply source 176 (see FIG. 7) prior to being used in the structural health monitoring system 170 for monitoring structural health 172 of the structure 30. The nanoparticle ink based piezoelectric sensors 110 may be coupled to the power and communication wire assembly 140 formed from a conductive ink 168 deposited onto the substrate 101 via the ink deposition process 122 prior to being used in the structural health monitoring system 170. Two or more nanoparticle ink based piezoelectric sensors 110 may be used to enable the structural health monitoring system 170.

The structure 30 may comprise an aircraft 10 (see FIG. 1), a spacecraft, an aerospace vehicle, a space launch vehicle, a rocket, a satellite, a rotorcraft, a watercraft, a boat, a train, an automobile, a truck, a bus, an architectural structure, a turbine blade, a medical device, electronic actuation equipment, a consumer electronic device, vibratory equipment, passive and active dampers, or another suitable structure. The system 170 and method 200 may be used across many industries including, for example, wind power generation (health monitoring of turbine blades), aerospace applications, military applications, medical applications, electronic actuation equipment, consumer electronic products, or any application where structures or materials require a monitoring system.

In another embodiment of the disclosure, there is provided a method of monitoring structural health 172 of a structure 30. The method comprises providing a structure 30 to be monitored for structural health 172. The method further comprises using a distributed network of nanoparticle ink based piezoelectric sensor assemblies 120 to sense and monitor the structural health 172 of the structure 30. The method further comprises providing electrical power to the distributed network of sensor assemblies 120 via an electrical power source 178. The method further comprises using a data communications network 179 to retrieve and process structural health data 174 of the structure 30 via one or more signals from the nanoparticle ink based piezoelectric sensor assemblies 120.

Embodiments of the system 170 and method 200 disclosed herein provide nanoparticle ink based piezoelectric sensors 110 for structural health monitoring that may be used for a variety of applications including ultrasonic damage detection for composite and metallic structures, crack propagation detection sensors, pressure sensors, or another suitable sensor. For example, the nanoparticle ink based piezoelectric sensors 110 of the system 170 and method 200 may provide cradle to grave health monitoring of various components in aircraft such as damage detection for door surrounds, military platforms such as crack growth detection for military aircraft, and space systems such as cryo-tank health monitoring. The nanoparticle ink based piezoelectric sensors 110 may provide structural health data that was previously not available that may influence new and efficient designs which may reduce costs.

Using the direct write printing process 124, and for example, the jetted atomized deposition process 126, along with the formulated nanoparticle ink, allows many nanoparticle ink based piezoelectric sensors 110 to be deposited onto a surface of a substrate 101 or a surface of a structure 30 and at a decreased cost as compared to known processes of depositing piezoelectric sensors. Embodiments of the system 170 and method 200 disclosed herein provide nanoparticle ink based piezoelectric sensors 110 that allow for the placement of the nanoparticle ink based piezoelectric sensors 110 in numerous areas of the structure 30 and in large quantities, both of which may be difficult with known piezoelectric sensors. Moreover, embodiments of the system 170 and method 200 disclosed herein provide nanoparticle ink based piezoelectric sensors 110 that are advantageous over known sensors because they may not require an adhesive to bond them to the substrate or structure, and this decreases the possibility that the nanoparticle ink based piezoelectric sensors 110 may disbond from the structure 30. Further, embodiments of the system 170 and method 200 disclosed herein provide nanoparticle ink based piezoelectric sensors 110 that are enabled by the availability of nanoscale ink particles 106 having favorable piezoelectric properties and that are deposited onto a substrate or structure in a desired configuration for use without the use of adhesive. Because the nanoparticle ink based piezoelectric sensors 110 may be deposited onto a substrate or structure with no adhesive between the sensors 110 and the substrate or structure, improved signal coupling into the structure being interrogated may be achieved. Further, embodiments of the system 170 and method 200 disclosed herein provide nanoparticle ink based piezoelectric sensors 110 that do not require manual placement or installation on the substrate or structure and may be deposited or printed onto the substrate or structure, along with all the required power and communication wire assemblies, thus decreasing labor and installation costs, as well as decreasing complexity and weight of the structure. In addition, the nanoparticle ink based piezoelectric sensors 110 may be deposited with numerous direct write printing processes, including the jetted atomized deposition process 126; may be fabricated from nanoparticle size particles which have been pre-crystallized and may be more efficient than known sensors that have not been crystallized; do not require a high temperature sintering/crystallization process and thus reduces or eliminates possible damage to temperature sensitive substrates or structures; may be deposited onto curved or non-planar substrates or structures; have no or minimal physical geometry limitations and thus decreases the possibility of inadequate sensing capacities or inadequate actuation responses. Further, embodiments of the system 170 and method 200 disclosed herein provide nanoparticle ink based piezoelectric sensors 110 that may be used to predict deterioration or weaknesses of the structure 30 prior to the actual development of such deterioration or weaknesses, and thus, may increase reliability of the structure or structural component parts, and may reduce overall manufacturing and maintenance costs over the life of the structure or structural component parts. Finally, embodiments of the system 170 and method 200 disclosed herein have the ability to predict, monitor, and diagnose the integrity, health, and fitness of a structure without having to disassemble or remove the structure or drill holes into the structure for insertion of any measurement tools.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A system for monitoring structural health of a structure, the system comprising:
   a structure to be monitored for structural health;
   a distributed network of nanoparticle ink based piezoelectric sensor assemblies deposited directly onto the structure with a nanoparticle ink deposited via an ink deposition direct write printing process, each assembly comprising:
   a plurality of nanoparticle ink based piezoelectric sensors; and,
   a plurality of conductive ink power and communication wire assemblies interconnecting the plurality of sensors;
   an ink deposition direct write printing apparatus depositing the distributed network of nanoparticle ink based piezoelectric sensor assemblies directly onto the structure and without use of an adhesive;
   an electrical power source providing electrical power to the distributed network; and,
   a data communications network retrieving and processing structural health data of the structure via one or more signals from the sensors.

2. The system of claim 1, further comprising a voltage supply source poling the plurality of nanoparticle ink based piezoelectric sensors.

3. The system of claim 1, wherein the structure comprises a material selected from a group comprising a composite material, a metallic material, and a combination of a composite material and a metallic material.

4. The system of claim 1, wherein the structure has a curved surface on which the distributed network of nanoparticle ink based piezoelectric sensor assemblies is deposited.

5. The system of claim 1, wherein the nanoparticle ink based piezoelectric sensors are deposited onto the structure in a customized shape.

6. The system of claim 1, wherein the ink deposition direct write printing apparatus comprises one of a jetted atomized deposition apparatus, an ink jet printing apparatus, an aerosol printing apparatus, a pulsed laser evaporation apparatus, a flexography printing apparatus, a micro-spray printing apparatus, a flat bed silk screen printing apparatus, a rotary silk screen printing process, and a gravure printing process.

7. The system of claim 1, wherein the distributed network of nanoparticle ink based piezoelectric sensor assemblies further comprises an insulation layer deposited directly onto a body of the structure comprising a metallic structure.

8. The system of claim 1, wherein each of the conductive ink power and communication wire assemblies comprises a first conductive electrode, a second conductive electrode, a first conductive trace wire, and a second conductive trace wire.

9. The system of claim 1, wherein the structural health data comprises disbonds, weak bonding, strain levels, moisture ingression, materials change, cracks, voids, delamination, porosity, and irregularities that adversely affect performance of the structure.

10. The system of claim 1, wherein the nanoparticle ink based piezoelectric sensors are comprised of nanoparticles having a particle size in a range of from about 20 nanometers to about 1 micron.

11. The system of claim 1, wherein the structure comprises an aircraft structure.

12. A method of monitoring structural health of a structure, the method comprising:
provising a structure to be monitored for structural health;
depositing directly onto the structure with a nanoparticle ink deposited via an ink deposition direct write printing process a plurality of nanoparticle ink based piezoelectric sensors and a plurality of conductive ink power and communication wire assemblies interconnecting the plurality of sensors to form a distributed network of nanoparticle ink based piezoelectric sensor assemblies;
providing electrical power to the distributed network via an electrical power source; and,
using a data communications network to retrieve and process structural health data of the structure via one or more signals from the sensors.

13. The method of claim 12, further comprising after depositing the plurality of nanoparticle ink based piezoelectric sensors, poling the nanoparticle ink based piezoelectric sensors with a voltage supply source to create an electric field across the nanoparticle ink based piezoelectric sensors.

14. The method of claim 12, wherein the ink deposition direct write printing process comprises one of a jetted atomized deposition process, an ink jet printing process, an aerosol printing process, a pulsed laser evaporation process, a flexography printing process, a micro-spray printing process, a flat bed silk screen printing process, a rotary silk screen printing process, and a gravure printing process.

15. The method of claim 12, wherein the data communications network retrieves data received from the nanoparticle ink based piezoelectric sensors with a receiver and processes data received from the nanoparticle ink based piezoelectric sensors with a computer processor.

16. The method of claim 12, wherein the structural health data comprises disbonds, weak bonding, strain levels, moisture ingression, materials change, cracks, voids, delamination, porosity, and irregularities that adversely affect performance of the structure.

17. A structure to be monitored for structural health, the structure comprising:
a body; and,
a distributed network of nanoparticle ink based piezoelectric sensor assemblies deposited directly onto the body of the structure with a nanoparticle ink deposited via an ink deposition direct write printing process, each assembly comprising:
a plurality of nanoparticle ink based piezoelectric sensors; and,
a plurality of conductive ink actuator assemblies interconnecting the plurality of sensors,
wherein a signal path within the distributed network comprises a plurality of nanoparticles and structural health data of the structure is obtained via one or more signals from the nanoparticle ink based piezoelectric sensors flowing through the signal path to a data communications network.

18. The structure of claim 17, wherein the structure has a curved surface on which the distributed network of nanoparticle ink based piezoelectric sensor assemblies is deposited.

19. The structure of claim 17, wherein the distributed network of nanoparticle ink based piezoelectric sensor assemblies further comprises an insulation layer deposited directly onto the body of the structure comprising a metallic structure.

20. The structure of claim 17, wherein the nanoparticle ink based piezoelectric sensors are comprised of nanoparticles having a particle size in a range of from about 20 nanometers to about 1 micron.

21. The structure of claim 17, wherein the ink deposition direct write printing process comprises one of a jetted atomized deposition process, an ink jet printing process, an aerosol printing process, a pulsed laser evaporation process, a flexography printing process, a micro-spray printing process, a flat bed silk screen printing process, a rotary silk screen printing process, and a gravure printing process.

22. The structure of claim 17, wherein the structure comprises an aircraft structure.

\* \* \* \* \*